(12) United States Patent
Whiteley et al.

(10) Patent No.: US 11,164,344 B2
(45) Date of Patent: Nov. 2, 2021

(54) PET IMAGE RECONSTRUCTION USING TOF DATA AND NEURAL NETWORK

(71) Applicant: Siemens Medical Solutions USA, Inc., Malvern, PA (US)

(72) Inventors: William Whiteley, Knoxville, TN (US); Vladimir Y. Panin, Knoxville, TN (US); Deepak Bharkhada, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 174 days.

(21) Appl. No.: 16/591,992

(22) Filed: Oct. 3, 2019

(65) Prior Publication Data

US 2021/0104079 A1 Apr. 8, 2021

(51) Int. Cl.
*G06T 11/00* (2006.01)
*A61B 6/03* (2006.01)
*G06N 3/08* (2006.01)
*G06T 7/00* (2017.01)

(52) U.S. Cl.
CPC ............ *G06T 11/005* (2013.01); *A61B 6/037* (2013.01); *G06N 3/08* (2013.01); *G06T 7/0012* (2013.01); *G06T 11/006* (2013.01); *G06T 2207/10104* (2013.01); *G06T 2207/20084* (2013.01)

(58) Field of Classification Search
CPC ....... A61B 6/032; A61B 6/037; A61B 6/5205; A61B 6/5235; G06T 7/0012; G06T 11/003; G06T 11/005; G06T 11/006; G06T 2207/10104; G06T 2207/20084
See application file for complete search history.

(56) References Cited

U.S. PATENT DOCUMENTS

| | | | |
|---|---|---|---|
| 8,000,513 B2 | 8/2011 | Defrise et al. | |
| 8,110,805 B2 | 2/2012 | Panin | |
| 9,990,741 B2 | 6/2018 | Panin | |
| 2015/0297168 A1 | 10/2015 | Panin | |
| 2018/0293762 A1* | 10/2018 | Fu | G06T 11/006 |
| 2020/0051260 A1* | 2/2020 | Shen | G06N 3/084 |

OTHER PUBLICATIONS

Joseph, Peter M., "An Improved Algorithim for Reprojecting Rays Through Pixel Images", IEEE Transactions on Medical Imaging, vol. MI-1, No. 3, Nov. 1982, 5pp.
Matej, Samuel, et al. Efficient 3-D TOF PET Reconstruction Using View-Grouped Histo-Images: DIRECT-Direct Image Reconstruction for TOF, IEEE Transactions on Medical Imaging, vol. 28, No. 5, May 2009, 13pp.
Ronneberger, Olaf, et al. "U-Net: Convolutional Networks for Biomedical Image Segmentation", Computer Science Department and BIOSS Centre for Biological Signalling Studies, University of Freiburg, Germany, http://lmb/informatik.uni-freiburg/de/, May 18, 2015, 8pp.

* cited by examiner

*Primary Examiner* — Katrina R Fujita

(57) ABSTRACT

A system and method include execution of a first scan to acquire a first PET dataset, back-projection of the first PET dataset to generate a first histo-image, input of the first histo-image to a trained neural network, and reception of a first output image from the trained neural network.

17 Claims, 9 Drawing Sheets

PET IMAGE RECONSTRUCTION USING TOF DATA AND NEURAL NETWORK

BACKGROUND

According to conventional Positron Emission Tomography (PET) imaging, a tracer compound including a radionuclide is introduced into a patient body by injection or ingestion. Radioactive decay of the radionuclide generates positrons, which eventually encounter electrons and are annihilated thereby. Annihilation produces two gamma photons which travel in approximately opposite directions. Accordingly, an annihilation event is identified when two detectors disposed on opposite sides of the body detect the arrival of two oppositely-travelling gamma photons within a particular coincidence time window.

Because the two gamma photons travel in approximately opposite directions, the locations of the two detectors determine a Line-of-Response (LOR) along which the annihilation event occurred. Time-of-flight (TOF) PET measures the difference between the detection times of the two gamma photons arising from the annihilation event. This difference may be used to estimate a particular position along the LOR at which the annihilation event occurred.

Recent increases in PET timing resolution have improved TOF-based determinations of event location. These events can be back-projected using Most Likely Annihilation (MLA) information to obtain an image of expected distribution referred to as a histo-image. Due to uncertainties in the determinations of event location, and the large compression ratio between the TOF data and the histo-image, the histo-image is typically blurred and unsuitable for most uses. Deblurring kernels applicable to a single histo-image are known but produce inferior image quality. Some systems perform MLA back-projections of different view data to generate multiple histo-images, deblur each histo-image individually using a deblurring kernel, and combine the deblurred histo-images into a single reconstructed image. These systems are computationally and memory intensive.

DETAILED DESCRIPTION

The following description is provided to enable any person in the art to make and use the described embodiments and sets forth the best mode contemplated for carrying out the described embodiments. Various modifications, however, will remain apparent to those in the art.

Generally, some embodiments provide a neural network which deconvolves a (blurred) histo-image to obtain a simulated reconstructed PET image. The histo-image may be generated from TOF sinograms using TOF back-projection, or directly from PET event data by back-projecting each recorded event. The neural network may be trained using PET images which were reconstructed from PET raw data (e.g., list mode or TOF sinograms) using conventional reconstruction techniques.

Figure 1:
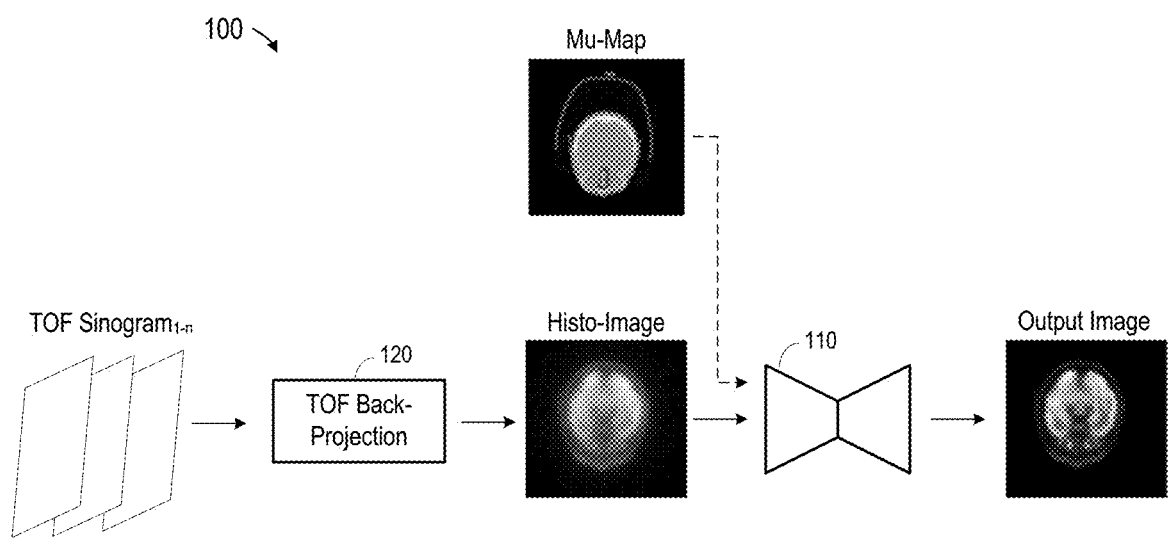
FIG. 1 is a block diagram of a system to generate a reconstructed PET image based on TOF sinograms and optional mu-maps according to some embodiments.

FIG. 1 is a block diagram of a deployed system according to some embodiments. System 100 includes trained network 110. Training of network 110 according to some embodiments will be described below. Although depicted as a neural network, network 110 and all neural networks referred to herein may comprise any type of processing system to implement a function. For example, network 110 may comprise a software application programmed to implement a function generated via prior neural network training as described below. Network 110 and all neural networks described herein may comprise hardware and software specifically-intended for executing algorithms based on a specified network architecture and trained network parameters.

In operation, TOF sinograms$_{1-n}$ are acquired as is known in the art. For example, TOF sinograms$_{1-n}$ may be acquired by a PET scanner after injection of a radioactive tracer into a subject volume (e.g., a patient or a phantom). Each of TOF sinograms$_{1-n}$ corresponds to a respective location over which coincident annihilation events within the volume were detected. Each TOF sinogram$_{1-n}$ stores the location of the LOR of each coincidence event such that all the LORs passing through a single point in the volume trace a sinusoid curve in the sinogram.

A sinogram is a data array of the angle versus the displacement of each LOR. Each of TOF sinograms$_{1-n}$ includes one row containing the LOR for a particular azimuthal angle φ. Each of these rows corresponds to a one-dimensional parallel projection of the tracer compound distribution at a different coordinate.

TOF back-projection component 120 applies a back-projection algorithm to TOF sinograms$_{1-n}$ as is known in the art to generate a histo-image. TOF back-projection component 120 may apply Joseph's method (P. M. Joseph, "An improved algorithm for reprojecting rays through pixel images," *IEEE Transactions on Medical Imaging*", vol. 1, no. 3, pp. 192-196, November 1982) to generate the histo-image as is known in the art. The generated histo-image is then input to trained network 110.

Generally, medical images are created by determining the attenuation caused by the subject tissue. This determination is relatively straightforward in the case of imaging modalities which transmit radiation through the body (e.g., Computed Tomography (CT)), since the amount of the external source radiation being transmitted through the body and the amount received at the detector are both known. However, the determination of attenuation in PET imaging is more difficult, because the amount of radiation being emitted by the emission source(s) within the body cannot be measured directly.

Accordingly, PET image reconstructions often incorporate attenuation corrections to generate improved images. The most common attenuation corrections are based on Linear Attenuation Coefficient (LAC) maps ("mu-maps") derived from a CT scan of the subject tissue. A transform is applied to the CT data to generate a mu-map. Several techniques exist generating a mu-map from CT data.

The dashed line of FIG. 1 depicts the optional input of a mu-map corresponding to the generated histo-image to trained network 110 in some embodiments. The mu-map may be derived from a CT scan performed during a same imaging session as the PET scan from which the TOF sinograms$_{1-n}$ were derived, as is known in the art. Inclusion of the mu-map may provide higher quality images than otherwise, due to the additional structural information provided by the mu-map to network 110.

Network 110 applies its trained function to the histo-image (and optional corresponding mu-map) to generate an output image. Input of a corresponding mu-map assumes that network 110 was trained using such mu-maps. By virtue of the trained function, and according to some embodiments, the output image will be similar in quality and resolution to ground-truth images used to train network 110. However, the output image may be obtained significantly faster and using fewer processing resources than conventional image reconstruction. Moreover, if the ground-truth images are of superior quality to conventional image reconstruction, the output images will also be of superior quality.

The input images and output images described herein may consist of single two-dimensional images or of three-dimensional volumes consisting of stacks of two-dimensional images.

Figure 2:
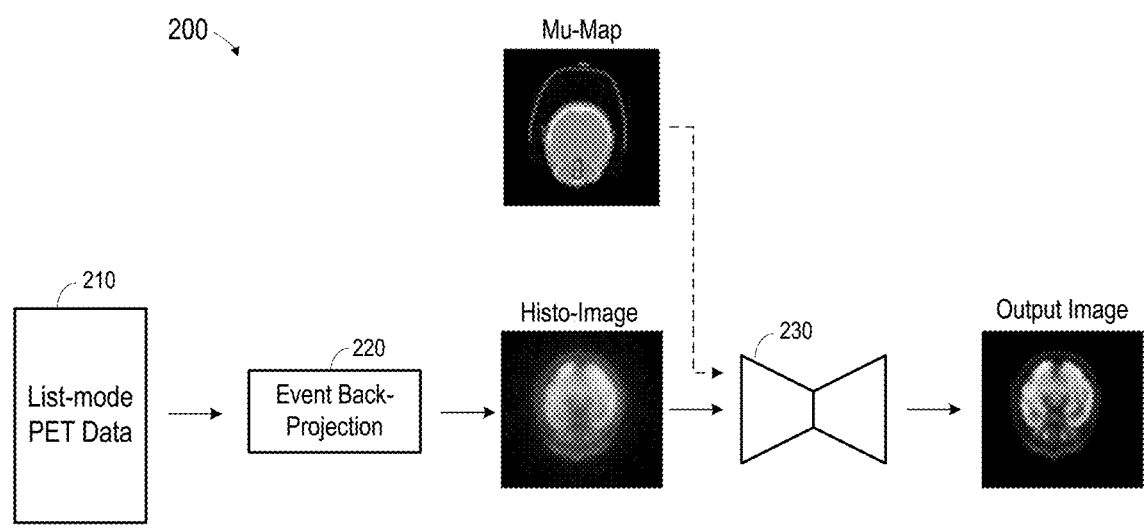
FIG. 2 is a block diagram of a system to generate a reconstructed PET image based on PET event data and optional mu-maps according to some embodiments.

FIG. 2 is a block diagram of a deployed system according to some embodiments. System 200 includes trained network 230 which, similar to network 110 of system 100, operates to generate an output image based on an input histo-image. Unlike the deployment of network 110, the histo-image is generated by back-projecting each event specified in list-mode PET data 210.

More specifically, a PET scanner acquires list-mode data 210 as is known in the art. List-mode data 210 includes the coordinates of each detected coincidence event. Event back-projection component 220 applies a back-projection algorithm to each event of list-mode data 210 generate a histo-image. Generally, the back-projection algorithm assigns every event to an image voxel along the LOR, according to its timing information. The histo-image generated by back-projecting list-mode data 210 may be more accurate than a histo-image generated by back-projecting sinograms generated from list-mode data 210 because list mode data exhibits higher-resolution timing data than TOF sinogram data generated therefrom. The generated histo-image is then input to trained network 230. Optionally, as described above, a mu-map corresponding to the histo-image may also be input to network 230.

Network 230 applies its trained function to the histo-image (and optional mu-map) to generate an output image. Due to the training of network 230, as will be described below, the output image is similar to the ground-truth images used to train network 230. Again, the output image may be obtained significantly faster and using fewer processing resources than conventional image reconstruction, and may be of superior quality to images obtained via conventional image reconstruction if the ground-truth images are of such superior quality.

With respect to FIGS. 1 and 2, events in list-mode format or LORs in TOF sinograms may be corrected using attenuation correction and normalization factors before back-projecting to obtain a modified histo-image. In such cases, the modified histo-image will serve as input to the neural network rather than the above-described histo-image.

Each functional component described herein may be implemented in computer hardware, in program code and/or in one or more computing systems executing such program code as is known in the art. Such a computing system may include one or more processing units which execute processor-executable program code stored in a memory system.

Figure 3:
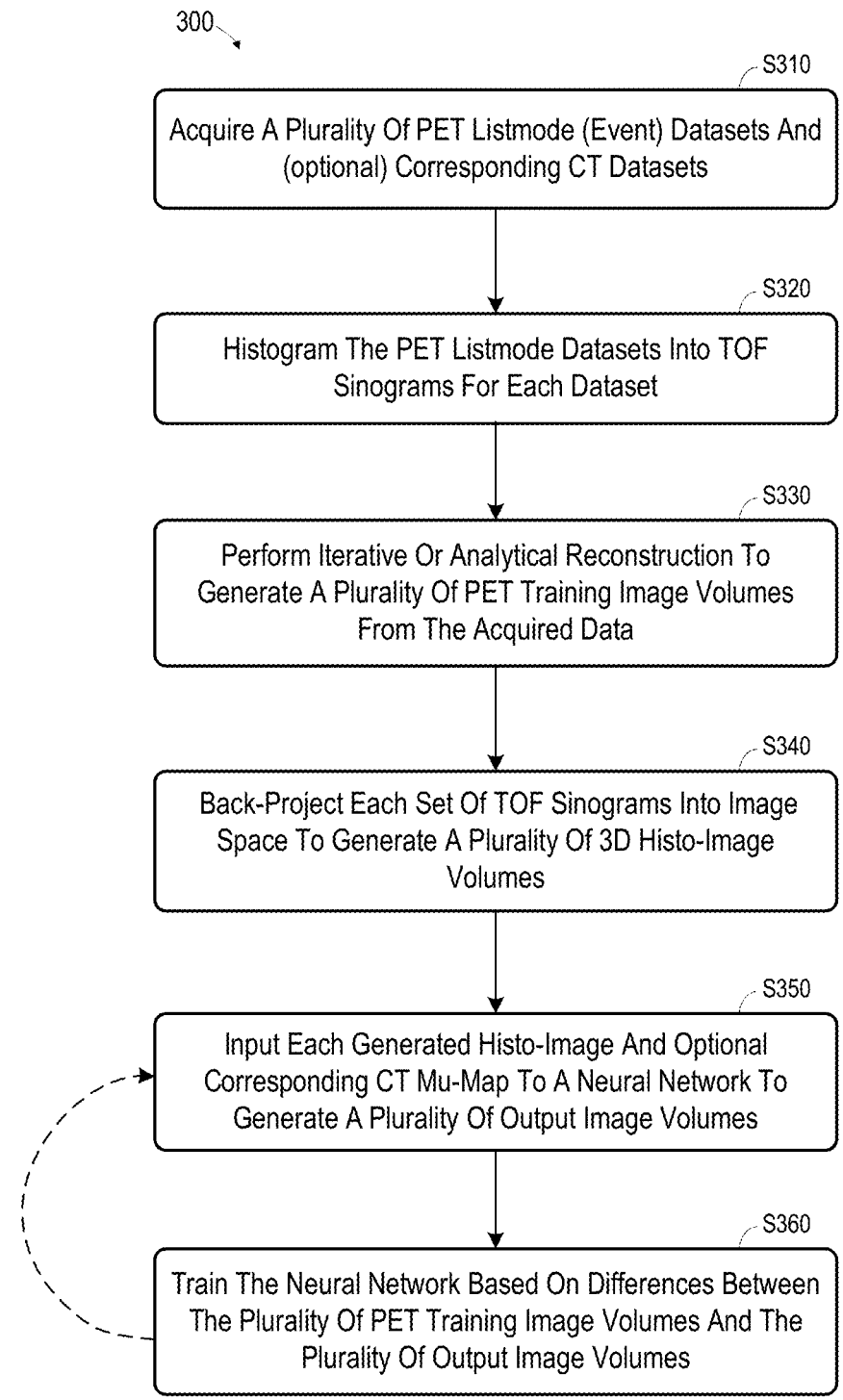
FIG. 3 is a flow diagram of a process to train a network to generate a reconstructed PET image based on TOF sinograms according to some embodiments.

FIG. 3 is a flow diagram of process 300 to train a neural network according to some embodiments. Process 300 will be described with respect to a training a network such as network 110, but embodiments are not limited thereto.

Flow diagram 300 and other processes described herein may be executed using any suitable combination of hardware and software. Software program code embodying these processes may be stored by any non-transitory tangible medium, including a fixed disk, a volatile or non-volatile random-access memory, a DVD, a Flash drive, and a magnetic tape. Embodiments are not limited to the examples described below.

Initially, a plurality of PET datasets are acquired at S310. The acquired PET datasets consist of PET acquisitions of list-mode data as is known in the art. The list-mode data contains the approximate location of each detected event. An optional corresponding CT dataset may also be acquired at S310 for each PET dataset as is known in the art. As described above, each CT dataset may be used to derive a mu-map providing structural information associated with its corresponding PET dataset.

The datasets acquired at S310 need not be acquired temporally adjacent to the remaining steps of process 300. According to some embodiments, the datasets are acquired from a repository of PET datasets. The acquired datasets may depict any type of volumes and may have been acquired using any number of PET scanners and PET acquisition settings. In some embodiments, the acquired PET datasets are associated with a same volume (e.g., anatomical region), PET scanner and PET acquisition parameters as will be imaged/utilized using the network trained according to process 300.

At S320, each of the acquired PET datasets is histo-grammed into TOF sinograms as is known in the art. Next, at S330, training image volumes are generated by reconstructing the raw PET data (list-mode or sinogram) using any reconstruction algorithm that is or becomes known. Examples of such algorithms may include filtered back-projection (FBP) and ordered-subsets expectation maximization (OSEM). As is known in the art, the raw PET data may be subjected to various data processing algorithms (attenuation correction, motion correction, denoising, etc.) prior to reconstruction.

Figure 4:
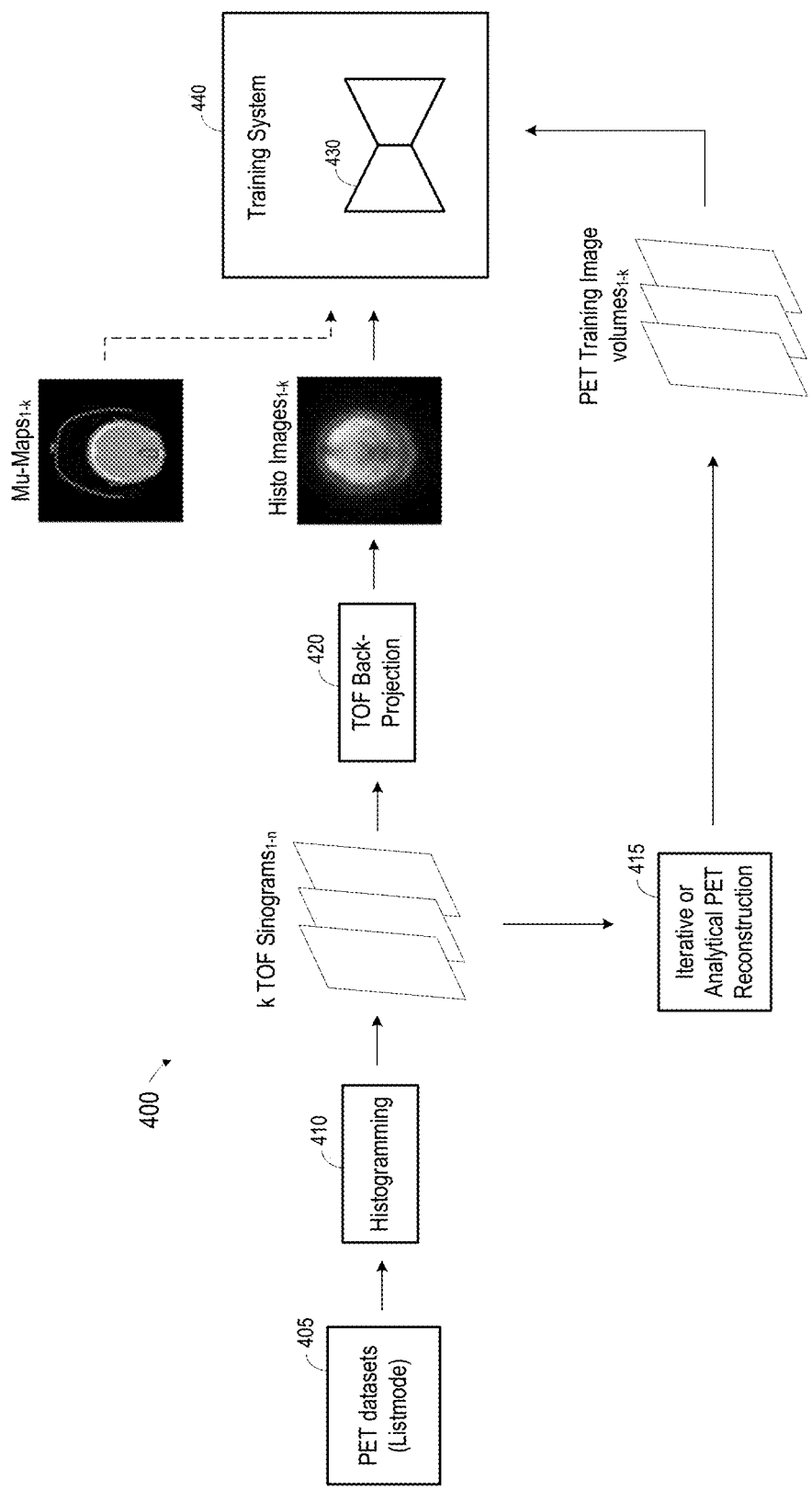
FIG. 4 illustrates training of a network to generate a reconstructed PET image based on TOF sinograms according to some embodiments.

FIG. 4 illustrates training architecture 400 according to some embodiments. Training architecture 400 depicts one example of process 300. As shown, PET datasets 405 are acquired at S310 and histogrammed by component 410 into k TOF sinograms$_{1-n}$ at S320. FIG. 4 also depicts PET reconstruction by component 415 of k TOF sinograms$_{1-n}$ into PET training (i.e., ground-truth) image volumes$_{1-k}$.

Next, at S340, each set of TOF sinograms is back-projected into image space to generate a three-dimensional histo-image volume corresponding to each set of TOF sinograms. The TOF back-projection may be performed at S340 using Joseph's method. FIG. 4 illustrates back-projection of k TOF sinograms$_{1-n}$ into histo-images$_{1-k}$ by TOF back-projection component 420.

Each histo-image (and, optionally, each corresponding mu-map) is input into a neural network at S340 to generate a plurality of output image volumes. That is, the neural network generates a single output image volume based on each input histo-image volume. At S360, the neural network is trained based on differences between the plurality of output image volumes and corresponding ones of the plurality of PET training image volumes. Flow continues to cycle between S350 and S360 until training is deemed to be complete.

Training system 440 may employ any type of neural network training that is or becomes known. Generally, training system 440 may determine a loss based on a comparison between k output image volumes generated by network 430 and corresponding ones of PET training image volumes$_{1-k}$. The loss may comprise an L1 loss, and L2 loss, or any other suitable measure of total loss. An L1 loss is the sum of the absolute differences between each output image and its corresponding ground truth PET image, and an L2 loss is the sum of the squared differences between each output image and its corresponding ground truth PET image.

The determined loss is back-propagated to network 430. Network 430 changes its internal weights, or kernel parameter values, based on the back-propagated loss as is known in the art. The process of S350 and S360 may repeat until it is determined that the loss has reached an acceptable level or training otherwise terminates. At termination, network 430 may be considered trained. Conceptually, network 430 has been trained to perform the reconstruction of the target PET images based on corresponding histo-images. In some embodiments, the function implemented by now-trained network 430 (e.g., embodied in parameter values of trained convolutional kernels) may then be deployed as shown in FIG. 1.

Figure 5:
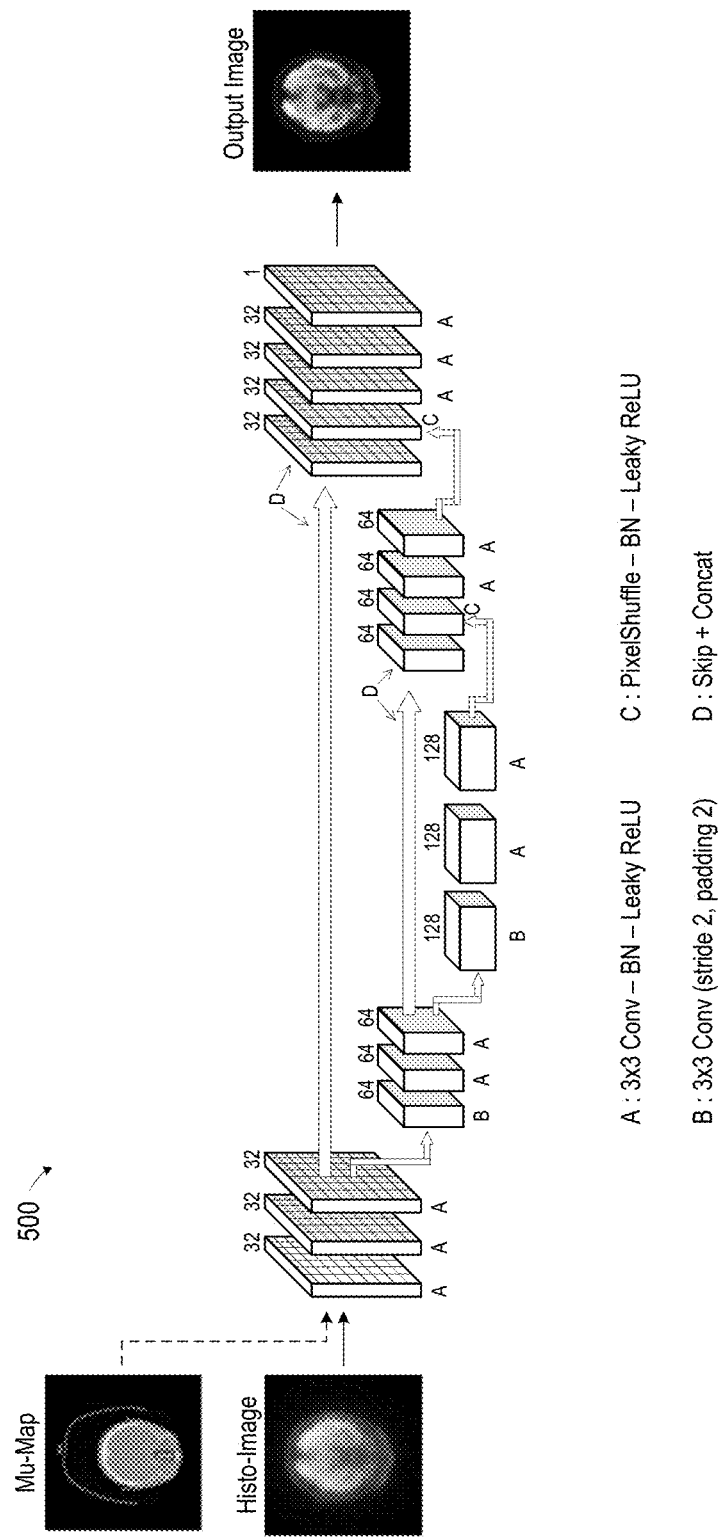
FIG. 5 illustrates a convolutional neural network architecture according to some embodiments.

The neural networks described herein may be implemented using any neural network architecture that is or becomes known. FIG. 5 illustrates neural network architecture 500 according to some embodiments. Architecture 500 is similar to a U-NET architecture but is fully convolutional. Specifically, the pooling of the U-Net architecture has been replaced with strided convolution and "up-convolution" has been replaced with the PixelShuffle upsampling method. Embodiments are not limited to the specific elements of architecture 500.

According to some embodiments, training is performed at S350 and S360 using the Adam optimizer to minimize a balanced combination of mean absolute error (MAE) and multi-scale structural similarity difference (SSIM Δ) between a target PET image $x_i^*$ and the output image $x_i=F_r(y_i)$ from histo-image $y_i$, with each image containing p pixels. A corresponding loss function is shown below.

$$MAE = \frac{1}{p}\sum_{i=0}^{p-1}\left|x_i - x_i^*\right|$$

$$SSIM\Delta = 1 - \frac{(2\mu_x * \mu_x + c_1)(2\sigma_x * \sigma_x + c_2)}{(\mu_{x^*}^2 + \mu_x^2 + c_1)(\sigma_{x^*}^2 + \sigma_x^2 + c_2)}$$

$$\alpha = \frac{\sum_{j=1}^{i+n-1} MAE_j}{\sum_{j=1}^{i+n-1} MAE_j + \sum_{j=1}^{i+n-1} SSIM\Delta_j}$$

$$Loss = (1-\alpha)MAE + \alpha SSIM\Delta$$

The above loss function dynamically balances the minimization of the absolute error between each corresponding pixel (i.e., MAE) and the perceptual loss function (SSIM), which evaluates the mean μ, variance σ2 and covariance σ between the images. A running average of n samples of each loss type is used to calculate a balancing loss scalar α at each training step.

Figure 6:
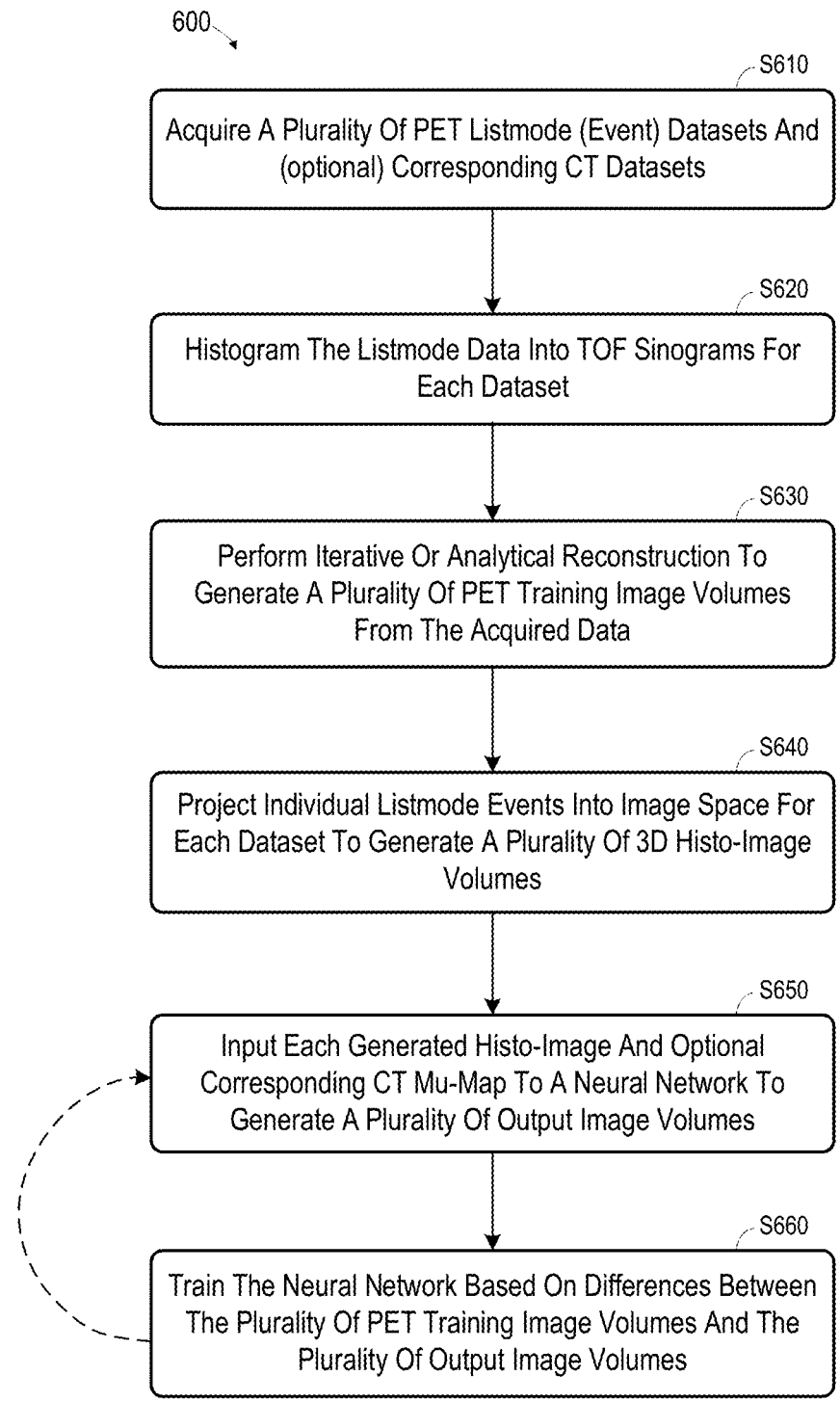
FIG. 6 is a flow diagram of a process to train a network to generate a reconstructed PET image based on PET event data according to some embodiments.

FIG. 6 is a flow diagram of process 600 to train a neural network to generate a simulated reconstructed PET image based on PET event data according to some embodiments. Accordingly, process 600 may be performed to train network 230 of system 200.

S610 and S620 may be performed as described above with respect to S310 and S320, but embodiments are not limited thereto. Specifically, a plurality of PET datasets consisting of PET acquisitions of list-mode data are acquired at S610. An optional corresponding CT dataset may also be acquired for each PET dataset at S610.

Each of the acquired PET datasets is histogrammed into TOF sinograms at S620 as is known in the art. Next, at S630, PET training image volumes are generated by reconstructing the raw PET data (list-mode or sinogram) using any reconstruction algorithm that is or becomes known.

Figure 7:
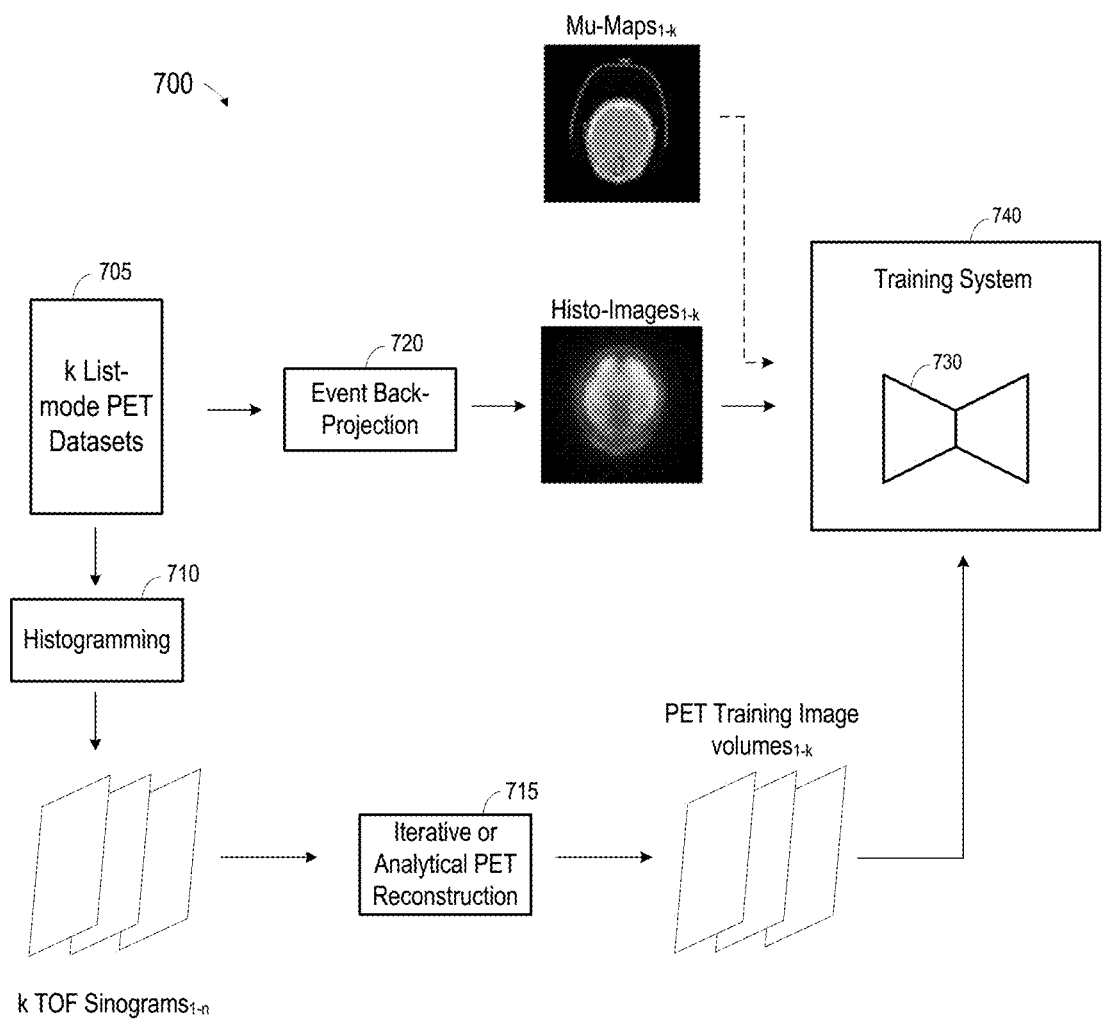
FIG. 7 illustrates training of a network to generate a reconstructed PET image based on PET event data according to some embodiments.

FIG. 7 illustrates training architecture 700 according to some embodiments of process 600. As shown, k list-mode PET datasets 705 acquired at S610 are histogrammed using component 710 into k TOF sinograms$_{1-n}$. Also, in the illustrated example, reconstruction component 715 generates PET training image volumes$_{1-k}$ from k TOF sinograms$_{1-n}$.

Next, at S640, event back-projection is performed on each set of list-mode data to generate a histo-image corresponding to each set. Event back-projection at S640 may, for example, be performed using the above-mentioned MLA or Joseph's method algorithms. FIG. 7 further illustrates back-projection of k sets of list-mode datasets 705 into histo-images$_{1-k}$ by event back-projection component 720.

Each histo-image (and, optionally, corresponding mu-map) is input into a neural network at S650 to generate a plurality of output image volumes. Neural network 730 may conform to architecture 500 or to any suitable network architecture. Then, at S660, the neural network is trained (e.g., using training system 740) based on differences between the plurality of output image volumes and corresponding ones of the plurality of PET training image volumes. S650 and S660 may be executed and re-executed as described above with respect to S350 and S360 until training is deemed to be complete.

According to some embodiments, thusly-trained neural network 730 implements a function of its inputs. The function may be characterized as a set of parameter values associated with each network node. The function may be deployed as is known in the art to an external system such as system 200 of FIG. 2. In one example, the training generates parameter values for kernels of a fully convolutional network. Another fully convolutional network comprising thusly-parameterized kernels may be efficiently incorporated within a system such as system 200 to generate a reconstructed image as described herein.

Figure 8:
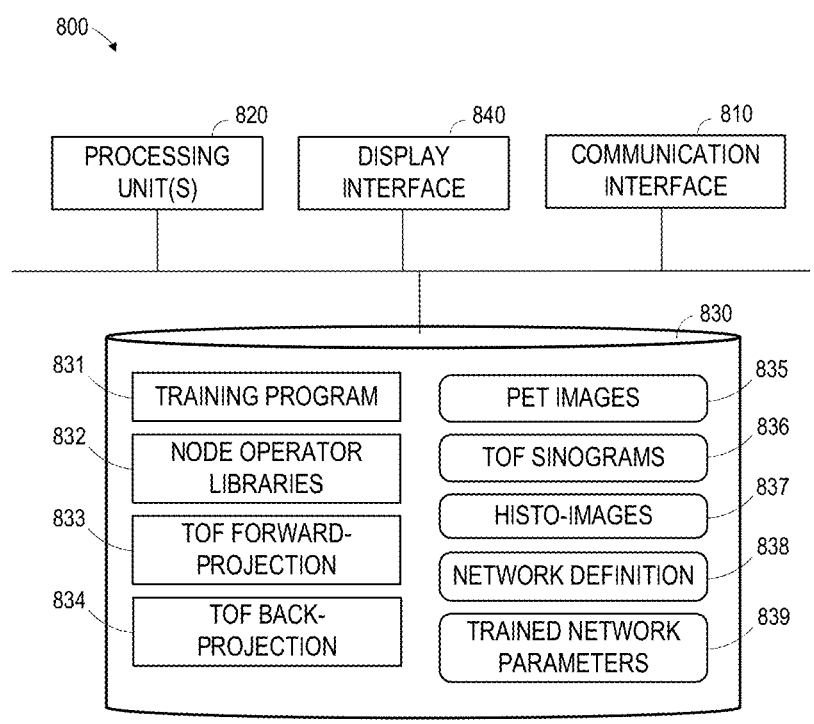
FIG. 8 is a block diagram of a system to train a network to generate a reconstructed PET image based on TOF sinograms according to some embodiments.

FIG. 8 illustrates computing system 800 according to some embodiments. System 800 may comprise a computing system to facilitate the design and training of an artificial neural network as is known in the art. Computing system 800 may comprise a standalone system, or one or more elements of computing system 800 may be located in the cloud.

System 800 includes communication interface 810 to communicate with external devices via, e.g., a network connection. Processing unit(s) 820 may comprise one or more processors, processor cores, or other processing units to execute processor-executable process steps. In this regard, storage system 830, which may comprise one or more memory devices (e.g., a hard disk drive, a solid-state drive), stores processor-executable process steps of training program 831 which may be executed by processing unit(s) 830 to train a network as described herein.

Training program 831 may utilize node operator libraries 832, which include code to execute various operations associated with node operations. According to some embodiments, computing system 800 provides interfaces and development software (not shown) to enable development of training program 831 and generation of network definition 838 which specifies the architecture of the neural network to be trained. Storage device 830 may also include, with reference to the elements of FIG. 4, program code 833 of TOF forward-projection component 410 and program code 834 of TOF back-projection component 420.

Data used for training the network may also be stored in storage device 830, including but not limited to acquired ground-truth PET images 835, TOF sinograms 836 generated therefrom, and histo-images 837 as described with respect to FIG. 4. Once trained, the parameters of the neural network may be stored as trained network parameters 839. As mentioned above, these trained parameters may be deployed in other systems as is known in the art to provide the trained functionality.

Figure 9:
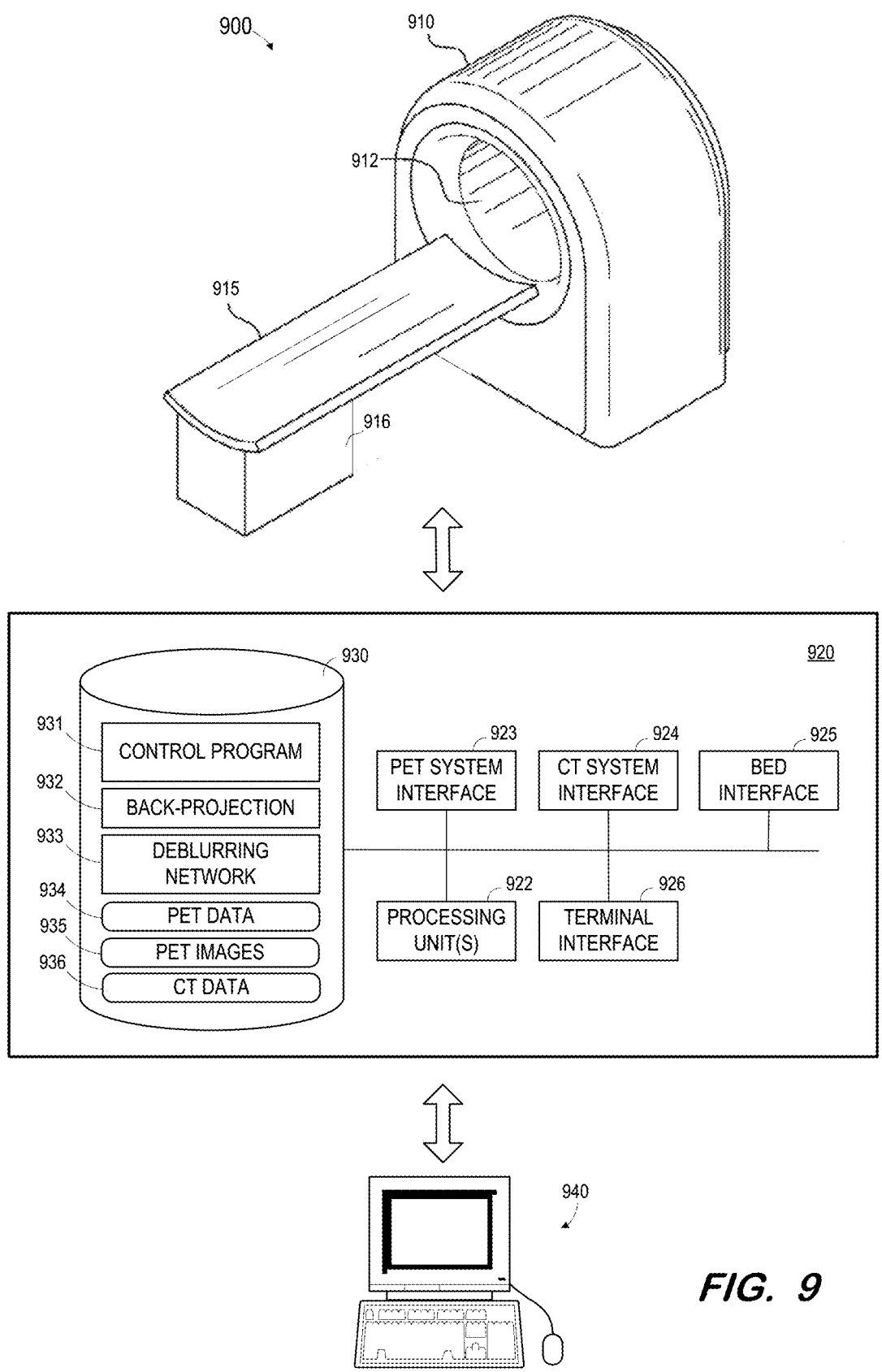
FIG. 9 illustrates a PET/CT imaging system according to some embodiments.

FIG. 9 illustrates PET/CT system 900 to execute one or more of the processes described herein. Embodiments are not limited to system 900.

System 900 includes gantry 910 defining bore 912. As is known in the art, gantry 910 houses PET imaging components for acquiring PET image data and CT imaging components for acquiring CT image data. The PET imaging components may include any number of gamma cameras in any configuration as is known in the art. The CT imaging components may include one or more x-ray tubes and one or more corresponding x-ray detectors.

Bed 915 and base 916 are operable to move a patient lying on bed 915 into and out of bore 912. In some embodiments, bed 915 is configured to translate over base 916 and, in other embodiments, base 916 is movable along with or alternatively from bed 915.

Movement of a patient into and out of bore 912 may allow scanning of the patient using the CT imaging elements and the PET imaging elements of gantry 910. Such scanning may proceed based on scanning parameters such as scan ranges and corresponding scanning speeds. Bed 915 and base 916 may provide continuous bed motion, as opposed to step-and-shoot motion, during such scanning according to some embodiments.

Control system 920 may comprise any general-purpose or dedicated computing system. Accordingly, control system 920 includes one or more processing units 922 configured to execute processor-executable program code to cause system 920 to operate as described herein, and storage device 930 for storing the program code. Storage device 930 may comprise one or more fixed disks, solid-state random-access memory, and/or removable media (e.g., a thumb drive) mounted in a corresponding interface (e.g., a USB port).

Storage device 930 stores program code of control program 931. One or more processing units 922 may execute control program 931 to, in conjunction with PET system interface 923, bed interface 925, and monitor interface 927, control hardware elements to move a patient into bore 912 and, during the movement, control gamma cameras to rotate around bore 912 and to detect coincidence events occurring within a body located in bore 912. The detected events may be stored in memory 930 as PET data 934, which may comprise list-mode data and/or sinograms.

One or more processing units 922 may also execute control program 931 to, in conjunction with CT system interface 924, cause a radiation source within gantry 910 to emit radiation toward a body within bore 912 from different projection angles, and to control a corresponding detector to acquire two-dimensional CT data. The CT data may be acquired substantially contemporaneously with the PET data as described above, and may be stored as CT data 936.

Back-projection program 932 may be executed to back-project acquired PET data to a histo-image as described with respect to systems 100 and 200. Deblurring network 933 may implement a trained function to convert the histo-image to a PET image as described above. Such PET images may be stored among PET images 935.

The PET images and CT images may be transmitted to terminal 940 via terminal interface 926. Terminal 940 may comprise a display device and an input device coupled to system 920. Terminal 940 may display PET images, CT images, histo-images, and/or any other suitable images or data. Terminal 940 may receive user input for controlling display of the data, operation of system 900, and/or the processing described herein. In some embodiments, terminal 940 is a separate computing device such as, but not limited to, a desktop computer, a laptop computer, a tablet computer, and a smartphone.

Each component of system 900 may include other elements which are necessary for the operation thereof, as well as additional elements for providing functions other than those described herein.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
a positron emission tomography (PET) imaging scanner to:
execute a first scan to acquire a first PET dataset; and
a processing system to:
back-project the first PET dataset to generate a first histo-image;
input the first histo-image to a trained neural network; and
receive a first output image from the trained neural network;
a Computed Tomography (CT) imaging scanner to execute a second scan to acquire a first CT dataset associated with the first PET dataset,
wherein the processing system is further adapted to:
generate a mu-map based on the first CT dataset; and
input the mu-map to the trained neural network with the first histo-image.

2. A system according to claim 1, wherein the trained neural network is a trained convolutional neural network.

3. A system according to claim 1, wherein the first PET dataset comprises a plurality of time-of-flight sinograms and the first output image is a reconstructed PET image.

4. A system according to claim 1, wherein the first PET dataset comprises list-mode data, and the first output image is a reconstructed PET image.

5. A system according to claim 1, wherein the neural network is trained based on a plurality of PET images reconstructed from the PET list-mode datasets and on a plurality of histo-images generated from the PET list-mode datasets.

6. A system according to claim 5, wherein generation of the plurality of histo-images comprises histogramming of the PET list-mode datasets into a plurality of sets of sinograms and back-projection of each of the plurality of sets of sinograms to generate the plurality of histo-images.

7. A method comprising:
executing a first scan to acquire a first positron emission tomography (PET) dataset;
back-projecting the first PET dataset to generate a first histo-image;
inputting the first histo-image to a trained neural network;
receiving a first output image from the trained neural network; and
acquiring a plurality of mu-maps, each of the plurality of mu-maps associated with a respective one of the plurality of PET list-mode datasets,
wherein inputting each of the plurality of histo-images to a neural network to generate a plurality of output images comprises inputting each of the plurality of mu-maps to the neural network.

8. A method according to claim 7, wherein the trained neural network is a trained convolutional neural network.

9. A method according to claim 7, wherein the first PET dataset comprises a plurality of time-of-flight sinograms and the first output image is a reconstructed PET image.

10. A method according to claim 7, wherein the first PET dataset comprises list-mode data, and the first output image is a reconstructed PET image.

11. A method according to claim 7, wherein the neural network is trained based on a plurality of PET images reconstructed from PET list-mode datasets and on a plurality of histo-images generated from the PET list-mode datasets.

12. A method according to claim 11, wherein generating the plurality of histo-images comprises histogramming the PET list-mode datasets into a plurality of sets of sinograms to generate the plurality of histo-images.

13. A method comprising:
acquiring a plurality of positron emission tomography (PET) list-mode datasets;
reconstructing each of the plurality of PET list-mode datasets into a PET image;
histogramming the PET list-mode datasets into a plurality of sinograms for each dataset;
back-projecting each of the plurality of sinograms for each dataset into image space to generate a plurality of histo-images, where each of the plurality of histo-images corresponds to a respective one of the plurality of PET images;
inputting each of the plurality of histo-images to a neural network to generate a plurality of output images;
modifying the neural network based on differences between the plurality of output images and respective ones of the plurality of PET images; and
acquiring a plurality of mu-maps, each of the plurality of mu-maps associated with a respective one of the plurality of PET list-mode datasets,
wherein inputting each of the plurality of histo-images to a neural network to generate a plurality of output images comprises inputting each of the plurality of mu-maps to the neural network.

14. A method according to claim 13, further comprising:
repeating the inputting and modifying until the differences satisfy a pre-specified criteria.

15. A method according to claim 14, wherein the pre-specified criteria is a minimized combination of mean absolute error and multi-scale structural similarity difference between each output image and a respective one of the plurality of PET images.

16. A method according to claim 13, wherein the plurality of sinograms comprise time-of-flight sinograms.

17. A method according to claim 13, wherein the neural network is a convolutional neural network which does not include pooling layers.

\* \* \* \* \*